(12) United States Patent  
Sahin Nomaler et al.

(10) Patent No.: US 9,011,001 B2
(45) Date of Patent: Apr. 21, 2015

(54) ROTATING RING APPARATUS (75) Inventors: Funda Sahin Nomaler, Eindhoven (NL); Johan Cornelis Compter, Eindhoven (NL); Arjan Franklin Bakker, Helenaveen (NL); Anthonius Johannes Dirk Verdel, Rotterdam (NL)

(73) Assignee: Koninklijke Philips N.V., Eindhoven (NL)

( * ) Notice: Subject to any disclaimer, the term of this patent is extended or adjusted under 35 U.S.C. 154(b) by 663 days.

(21) Appl. No.: 13/060,930

(22) PCT Filed: Aug. 31, 2009

(86) PCT No.: PCT/IB2009/053788
§ 371 (c)(1),
(2), (4) Date: Feb. 25, 2011

(87) PCT Pub. No.: WO2010/026523
PCT Pub. Date: Mar. 11, 2010

(65) Prior Publication Data
US 2011/0158382 A1    Jun. 30, 2011

(30) Foreign Application Priority Data
Sep. 4, 2008  (EP) .................................... 08163647

(51) Int. Cl.
*A61B 6/02*    (2006.01)
*F16C 32/04*   (2006.01)
(Continued)

(52) U.S. Cl.
CPC .... *F16C 32/0493* (2013.01); *G01N 2223/3303* (2013.01); *A61B 6/4435* (2013.01); *A61B 6/035* (2013.01); *F16C 2300/14* (2013.01); *H02K 7/09* (2013.01); *H02K 41/03* (2013.01)

(58) Field of Classification Search
CPC ............ A61B 6/02; A61B 6/03; A61B 6/032; A61B 6/035; A61B 6/40; A61B 6/4007; A61B 6/4014; A61B 6/44; A61B 6/4429; A61B 6/4435; A61B 6/56; G01N 2223/304; G01N 2223/308; G01N 2223/3303; G01N 2223/3304
USPC ................................ 378/4, 15, 197
See application file for complete search history.

(56) References Cited

U.S. PATENT DOCUMENTS

| 1,551,347 A |   | 8/1925 | Trombetta |
| 4,276,490 A | * | 6/1981 | Saldinger ....................... 310/184 |

(Continued)

FOREIGN PATENT DOCUMENTS

| DE | 20315369 U1 | 12/2003 |
| DE | 10304030 A1 | 9/2004 |

(Continued)

OTHER PUBLICATIONS

Cho et al: "An Investigation on the Characteristics of a Single-Sided Linear Induction Motor at Standstill for Maglev Vehicle"; IEEE Transactions on Magnetics, Mar. 1997, vol. 33, No. 2, pp. 2073-2076.

(Continued)

*Primary Examiner* — Thomas R Artman (57) ABSTRACT

The present invention relates to a rotating ring apparatus comprising: —a stationary ring (1), —a rotating ring (2) for rotation around a central region (3), —a rotation unit (4, 5) for radially bearing and rotating said rotating ring (2) with respect to the stationery ring (1), said rotation unit including a stationary induction element (4) mounted on said stationery ring (1) and a rotating induction element (5) mounted on said rotating ring (2), and —a controller (8) for controlling said rotation unit (4, 5) to rotate and levitate the rotating induction element (5).

20 Claims, 7 Drawing Sheets (51) Int. Cl.
    *A61B 6/00*     (2006.01)
    *A61B 6/03*     (2006.01)
    *H02K 7/09*     (2006.01)
    *H02K 41/03*    (2006.01)

(56) References Cited

U.S. PATENT DOCUMENTS

| | | | |
|---|---|---|---|
| 4,912,735 A * | 3/1990 | Beer | 378/15 |
| 4,942,597 A * | 7/1990 | Van Acker et al. | 378/197 |
| 5,179,583 A * | 1/1993 | Oikawa | 378/135 |
| 5,481,585 A | 1/1996 | Kimura et al. | |
| 5,493,599 A * | 2/1996 | Mattson | 378/147 |
| 5,631,944 A * | 5/1997 | Kimura et al. | 378/134 |
| 2002/0031201 A1 | 3/2002 | Suzuki et al. | |
| 2011/0158382 A1* | 6/2011 | Sahin Nomaler et al. | 378/21 |

FOREIGN PATENT DOCUMENTS

| | | |
|---|---|---|
| EP | 0017724 A1 | 10/1980 |
| EP | 0215523 A1 | 3/1987 |
| EP | 0588002 A1 | 3/1994 |
| EP | 0701391 A1 | 3/1996 |
| NL | 9401288 A | 3/1996 |
| SU | 965423 A1 | 10/1982 |
| WO | 02089671 A2 | 11/2002 |
| WO | 2004030542 A2 | 4/2004 |

OTHER PUBLICATIONS

Stickler, J.: "A Study of Single-Sided Linear Induction Motor Performance With Solid Iron Secondaries"; IEEE Transactions on Vehicular Technology, May 1982, vol. VT-31, No. 2, pp. 107-112.

Verdel, A.: "Decoupled Control of Thrust and Normal Forces of Linear Induction Motor for a Novel Magnetically Levitated System"; M. Sc. Graduation Paper—Graduation Symposium Jan. 2007—Dept. Electrical Engineering, TU/e-APT536-07-0278, pp. 1-10.

* cited by examiner

ROTATING RING APPARATUS

FIELD OF THE INVENTION

The present invention relates to a rotating ring apparatus, as, for instance, used in computer tomography (CT) scanner as gantry.

BACKGROUND OF THE INVENTION

In the gantry of a CT scanner air bearings are used to support the rotating parts of the gantry. Such a CT scanner is, for instance, disclosed in WO 2004/030542 A2, according to which a plurality of air bearing elements are interfacing a stationary gantry and a rotating gantry. To absorb vibrational energy and to damp air hammer vibrations a damping assembly is mounted to at least one lower bearing element.

Instead of air bearings it is also possible to use fluid bearings between the stationary gantry and the rotating gantry employing radial and axial fluid bearing pads, such as disclosed in WO 02/089671 A2. The fluid bearing provides a fluid barrier which separates the rotating gantry from the stationary gantry.

Those bearings are one of the major costly components in such a CT scanner and in other rotating ring apparatuses.

SUMMARY OF THE INVENTION

It is an object of the present invention to provide a rotating ring apparatus in which the generally used costly type of bearings, such as air bearings or fluid bearings, are replaced by other kinds of bearings providing at least the same main function without introducing other major problems such as mechanical instability, vibrations or noise.

In a first aspect of the present invention a rotating ring apparatus is presented comprising:
 a stationary ring,
 a rotating ring for rotation around a central region,
 a rotation unit for radially bearing and rotating said rotating ring with respect to the stationary ring, said rotation unit including a stationary induction element mounted on said stationary ring and a rotating induction element mounted on said rotating ring, and
 a controller for controlling said rotation unit to rotate and levitate the rotating induction element.

The present invention is based on the idea to replace the commonly used types of bearings, such as air bearings or fluid bearings, by magnetic levitation means, which is quite an economic alternative. In particular, according to present invention a rotation unit is provided including a stationary induction element and a rotating induction element. Thus, the invention makes use of the principle of electromagnetic induction to simultaneously levitate and rotate the rotating ring with respect to the stationary ring. Such magnetic levitation means provide the advantage that mechanical friction, wear, noise and vibrations are minimized, which extends the lifetime of the rotating ring apparatus.

Besides the reduction of the costs achieved by use of the magnetic levitation means, the present invention further has the advantage of an added active control possibility of the central point within the rotating ring, i.e. the rotation around this central point can be provided with high precision. This is advantageous in many applications of the rotating ring apparatus. For instance, when used in a CT scanner, the image quality of the images generated from the raw data acquired with such a CT scanner can be improved compared to the image quality achievable with known CT scanners.

Since the rotating induction element is both rotated and levitated by the rotation unit through electromagnetic induction, an appropriate controller is provided for controlling the rotation unit which, preferably, is adapted for simultaneous and decoupled control of thrust and normal forces.

Preferred embodiments of the invention are defined in the dependent claims.

In a preferred embodiment said stationary induction element comprises one or more, in particular two or three, arc-shaped induction sub-elements arranged at different angular positions around said central region. In this way, the arc-shaped induction sub-element(s) can be formed to optimally guide the magnetic flux and to distribute the torque and force components as desired around the circumference.

Further, said one or more induction sub-elements each comprises preferably a ferromagnetic core element, in particular having a toothed structure, and a plurality of electrically conductive windings wound within the core element, in particular within the toothed structure. Thus, a magnetic field distribution is generated along the stator segment by means of the current through said windings. The distribution of the windings helps to shape the sinusoidal magnetic flux waveform.

Still further, said one or more induction sub-elements each comprises preferably a single or double layer of windings. The double layer is more costly, but has the advantage that more sinusoidal magnetic flux density distribution in the air gap (between the stationary induction element and the rotating induction element) is increased.

According to another embodiment said rotation unit comprises a radial levitation unit, in particular a current controlled radial levitation unit. This provides for (additional) levitation, for instance to lift the rotating induction element or at least to support the lifting by use of the stationary induction element.

Such a radial levitation unit can, for instance, comprise an active or passive magnetic bearing unit, such as actuators comprising permanent magnets and/or windings for active control. One type of actuator can be implemented as an E-core shape actuator comprising an E-shaped ferromagnetic core, a coil wound around the central leg of the E-shaped core and a permanent magnet in the middle of the leg.

In a preferred embodiment the rotating induction element comprises a closed induction ring, which is integrally formed or segmented. The segmented form is advantageous due to ease of manufacturing and reduced costs Said induction ring can be implemented in different ways. For instance, the complete ring can be made of an electrically conductive material, it can comprise a first ring layer made of a single material, in particular ferromagnetic iron and/or steel, or it can comprise a first ring layer made of a first material, in particular Al or Cu, and a second ring layer made of a second material, in particular ferromagnetic iron and/or steel, the induction ring being arranged such that the first ring layer faces said stationary induction element. The different forms are related with the ease of manufacturing. Al, Cu and steel is the optimal form.

Preferably, the arrangement of the rotation unit is such that said rotating induction element is arranged at a larger radial distance from the central region than said stationary induction element, i.e. the rotating induction element rotates around said stationary induction element. But the arrangement can also be made the other way around. The particular arrangement mainly depends on the type of application and the general mechanical construction of the rotating ring apparatus. When used in a CT scanner, the first mentioned arrangement is preferred.

To support axial alignment axial bearing means are provided in an embodiment, in particular magnetic axial bearing means, for axially bearing said rotating ring with respect to said stationary ring.

In a particular application the rotating ring apparatus is used in a CT scanning apparatus further comprising a radiation source mounted on said rotating ring for rotation around an object placed in said central region and for emitting radiation in the direction of said object, and a detection unit for detecting radiation passed through said object and said central region. Preferably, the detection unit is mounted on said rotating ring. The invention is, however, not restricted to this type of application, but can generally be used for all applications where an element is rotated around a central region.

According to an advantageous embodiment said stationary induction element comprises at least two induction sub-elements arranged at different angular positions around said central region, wherein said controller is adapted to control the frequencies and the currents for control of levitation forces of said induction sub-elements in a decoupled way, in particular by controlling frequencies and currents provided to said induction sub-elements. Thus, a simultaneous and decoupled control of thrust and normal forces of the induction sub-elements can be provided.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
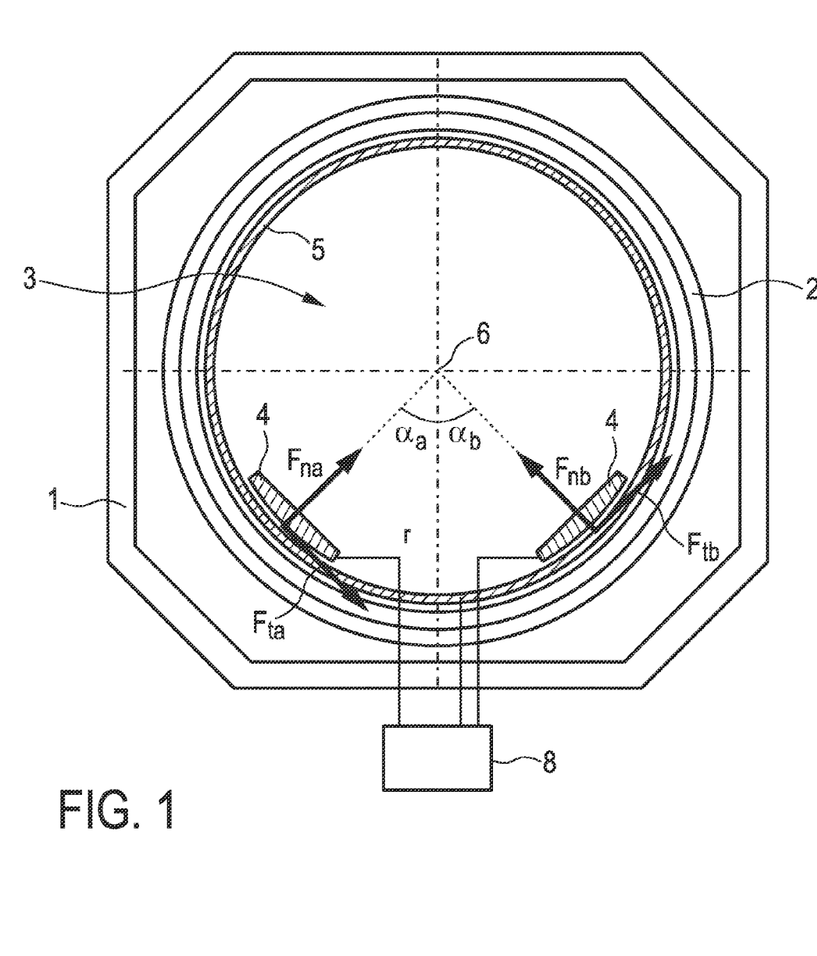
FIG. 1 shows a front view of a cross section through an embodiment of a rotating ring apparatus according to the present invention.
Figure 2:
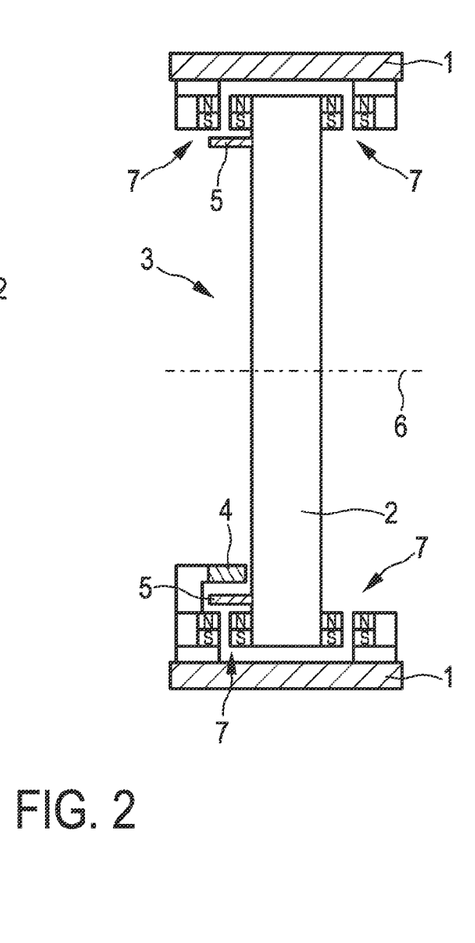
FIG. 2 shows a side view of a cross section through the rotating ring apparatus shown in FIG. 1.

FIG. 1 shows a front view of a cross section through an embodiment of a rotating ring apparatus according to the present invention. FIG. 2 shows a side view of a cross section through the same embodiment. The rotating ring apparatus comprises a stationary ring 1, a rotating ring 2 for rotation around a central region 3 and a rotation unit 4, 5 for radially bearing and rotating said rotating ring 2 with respect to the stationary ring 1. The rotation unit includes a stationary induction element 4 mounted on the stationary ring 1 and a rotating induction element 5 mounted on the rotating ring 2. The stationary ring 1, the rotating ring 2 and the rotation unit 4, 5 are all arranged coaxially with respect to a central axis 6.

For axially bearing the rotating ring 2 with respect to the stationary ring 1 axial bearing means 7 are provided in this embodiment, which are, for instance, implemented as a magnetic axial bearing unit. For control of the rotation unit 4, 5 so as to rotate and levitate the rotating induction element 5 a controller 8 is provided.

The present invention thus uses a magnetic levitation system through the use of linear induction motor (LIM) segments implemented in the rotating ring apparatus. In particular a single-sided LIM (SLIM) is used. Details thereof and the function of the apparatus will be explained below.

Magnetic suspension systems minimize mechanical friction, wear, noise and vibrations, which extends the lifetime of a machine. The rotating ring apparatus according to the present invention is levitated and rotated through the use of such SLIMs, which are represented by the rotation unit 4, 5 shown in FIGS. 1 and 2. In particular, such a SLIM comprises a stationary (primary) induction element 4 and a rotating (secondary) induction element 5.

In this embodiment two stationary induction elements 4 are used positioned under an angle $\forall_a$ and $\forall_b$, but it could also be only a single or more stationary induction elements 4.

Figure 3:
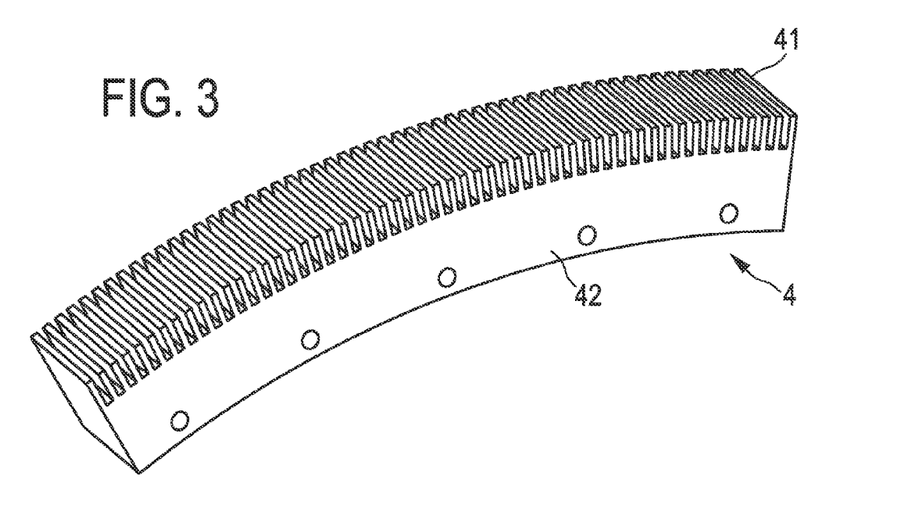
FIG. 3 shows a perspective view of an embodiment of a stationary induction element.

FIG. 3 shows an embodiment of an arc-shaped stationary induction element 4 without windings. The teeth 41 and the core 42 are, for instance, made of iron silicon laminated material having a pack of, for instance 200 laminations to prevent major influence of eddy currents in the stationary induction element 4. Increasing the number of poles improves the force capability, but also increases manufacturing complexity and thus rises the costs of such a stationary induction element 4. Among these design criteria a trade-off could be made so as to construct the element 4 with four pole pairs.

Figure 4:
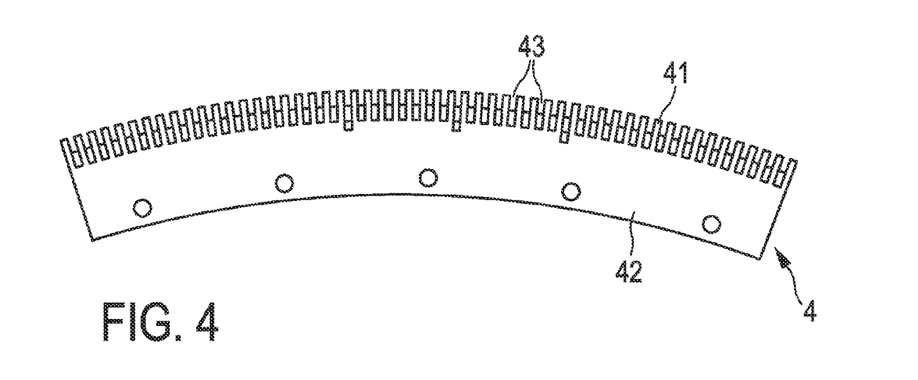
FIG. 4 shows a side view of the stationary induction element shown in FIG. 3.

A side view of the secondary induction element 4 shown in FIG. 3 including primary windings 43 is shown in FIG. 4. As can be seen a double layer of windings is provided in each slot between neighboring teeth 41. This improves the magnetic flux distribution and reduces the resistance and leakage reactance significantly. Also the half end slots at both ends of the secondary induction element 4 can be seen, which are ⅚ short pitched to eliminate the fifth and seventh order harmonics of the induced magnetic flux density, which could be a major disturbance. The total width of the stationary induction element 4 is given by the width of the core 42 and the width of the end windings, i.e. the windings exceeding the width of the core on both sides of the stationary induction element 4, resulting in a total width of the complete stationary induction element.

Figure 5:
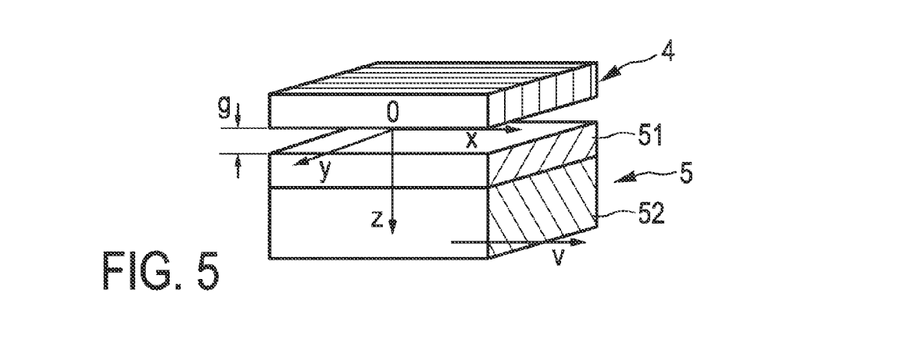
FIG. 5 shows a perspective view of the arrangement of the stationary induction element with respect to the rotating induction element.

An embodiment of the rotating induction element 5 is shown in the perspective view of FIG. 5 with respect to the stationary induction element 4. It comprises a non-ferromagnetic high conductive inner ring layer 51, e.g. made of aluminum or copper, backed up with a ferromagnetic second ring layer 52 (core layer), e.g. made of ferromagnetic iron and/or steel. It shall be noted here that it is possible that the rotating induction element 5 only comprises the second ring layer 52.

To produce a high magnetic flux density from a certain amount of current it is important to keep the height of the air gap g as small as possible, for instance at an amount of approximately 1 mm.

Figure 6:
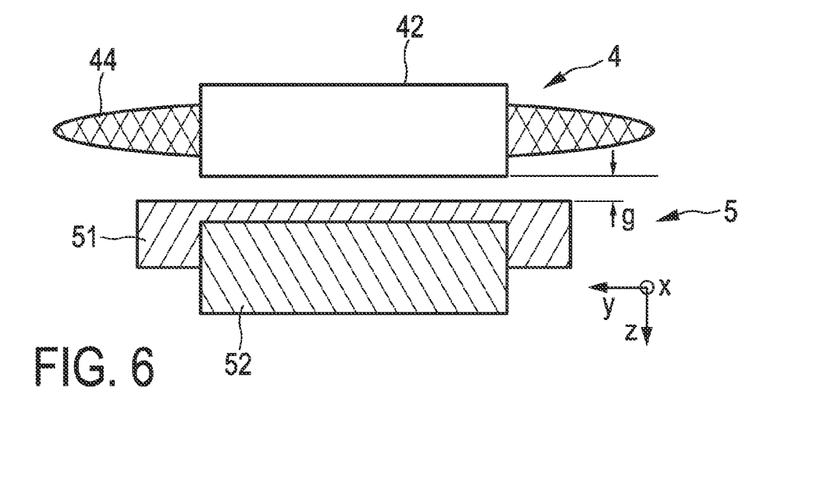
FIG. 6 shows a cross section through the arrangement of the stationary induction element with respect to the rotating induction element.

FIG. 6 shows a two-dimensional schematic cross section of the arrangement of the rotating induction elements with respect to the stationary induction element 4. As can be seen from this figure the end windings 44 of the windings 43 of the stationary induction element 4 extend over the core 42 and also have a broader width than the rotating ring element 4 in this embodiment.

The rotation unit provided according to the present invention uses the principle of an induction motor (asynchronous motor). 3-phase currents are provided to the windings 41 of the stationary induction element 4 by which induction eddy currents are induced in the first ring layer 51 of the rotating induction element 5. Thus a rotating magnetic field pattern is created. This changing magnetic field pattern induces currents in the conductors of the rotating induction elements, i.e. the first ring layer 51. These currents interact with the rotating magnetic field created by the stationary induction element 4 so that the rotating induction element 5 will turn.

Figure 7:
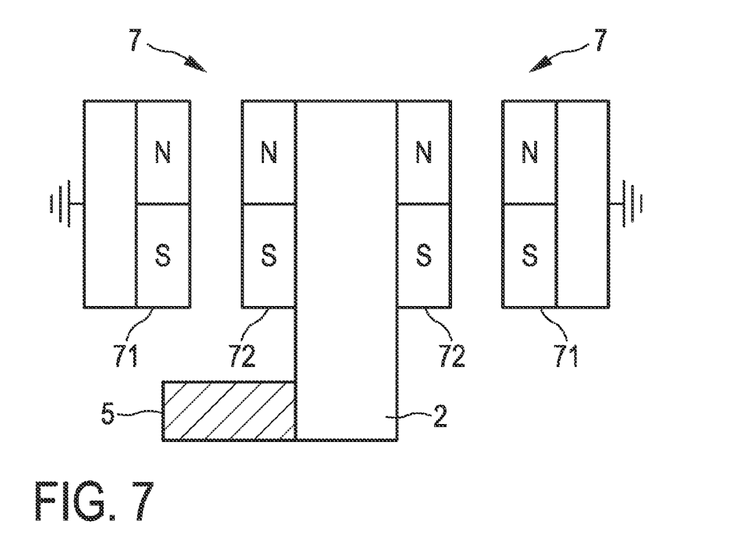
FIG. 7 shows a schematic set-up of axial bearings.

FIG. 7 shows an embodiment of magnetic axial bearing means 7 for axially bearing and providing axial stiffness of the rotating induction element 5. Each axial bearing 7 comprises two pairs of permanent magnets 71, 72, the first permanent magnet 71 being located fixed in space, e.g. mounted on the stationary ring 1 (see FIG. 2), and the second permanent magnet 72 being mounted on the rotating ring 2 and thus being rotatable together with the rotating induction element 5.

Simulations have shown that the maximal stiffness is found when the north and south pole of the permanent magnets 71, 72 are next to each other as shown in FIG. 7. The air gap width between the neighboring permanent magnets 71, 72 in each pair is set in an embodiment to 1.5 mm.

Figure 8:
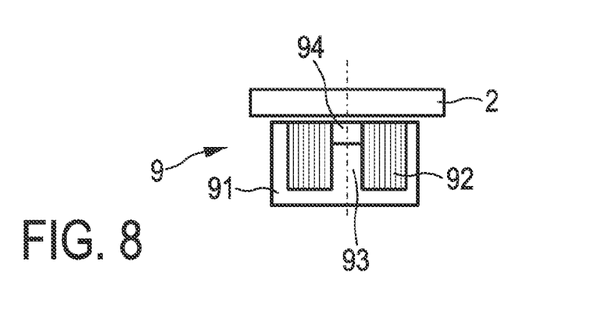
FIG. 8 shows an embodiment of a radial bearing.

To provide sufficient radial stiffness it is proposed to provide a radial levitation unit, in particular a current control levitation unit comprising one or more active or passive magnetic bearing units. An embodiment of such an active magnetic bearing unit is shown in FIG. 8. Preferably, two or more of those magnetic bearing units 9 are placed on the stationary ring 1 outside of the rotating ring 2 at different radial positions. In the embodiment shown in FIG. 8 the axial bearing unit 9 comprises an E-shaped ferromagnetic core element 91, a coil 92 wound around the central leg of the E-shaped core element 91 and a permanent magnet 94 placed at the end of the central leg 93 facing the rotating ring 2. The magnet 94 creates preload, and with current the amount of attraction force generated is adjusted.

The radial bearing elements 9 also have the function to lift the rotating ring 2 or at least to help lifting the rotating ring 2 together with the stationary and rotating induction elements 4, 5. In an embodiment these radial bearing elements 9 are radially positioned at the same angular position as the stationary induction elements 4. It shall be noted, however, that other positions and/or other implementations of radial bearing elements 9 can be used as well.

Figure 9:
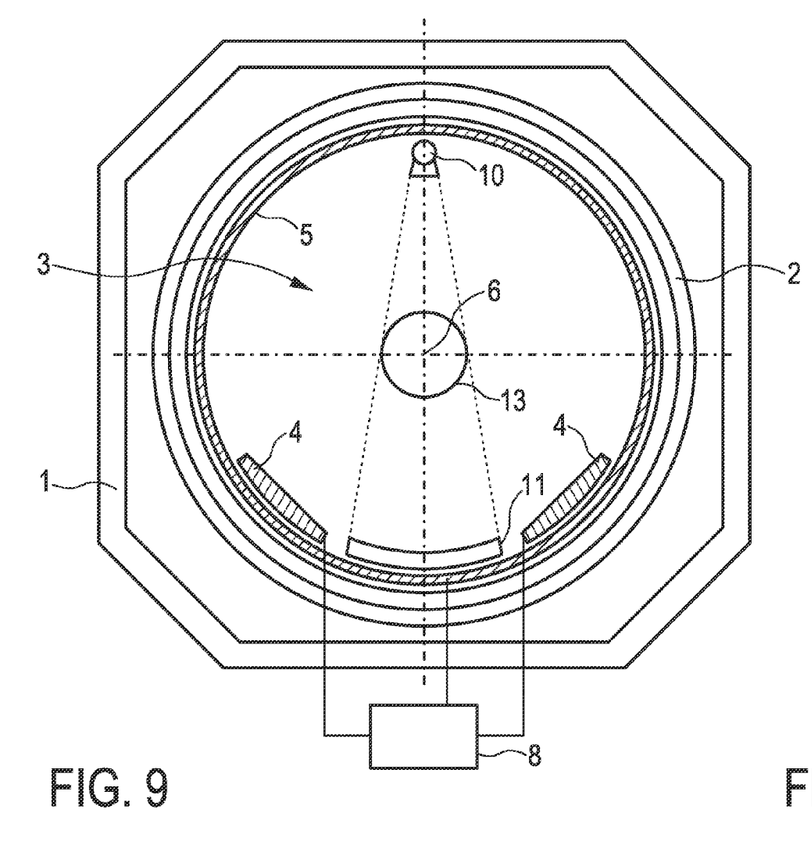
FIG. 9 shows a side view of a cross section through a rotating ring apparatus used in a CT scanner.
Figure 10:
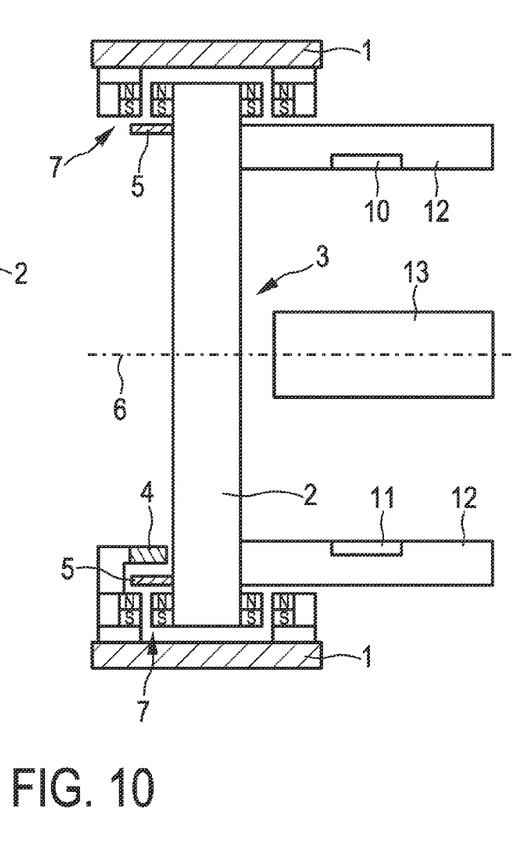
FIG. 10 shows a side view of cross section through the rotating ring apparatus shown in FIG. 9.

FIGS. 9 and 10 show cross sections through a further embodiment of a rotating ring apparatus according to the present invention provided with further elements for use in a CT scanner. In particular, besides the elements shown in the embodiment depicted in FIGS. 1 and 2, an X-ray source 10 and an X-ray detector 11 are provided, which are both mounted, via a support 12, on the rotating ring 2. Thus, in this embodiment both the X-ray source 10 and the X-ray detector 11 are rotated around the central region 3 in which an object 13, such as a patient or a workpiece, can be placed for obtaining X-ray images in the known manner.

It shall be noted that the thrust force in the embodiments shown in FIGS. 1, 2 and FIGS. 9, 10 can independently be controlled in either the positive or negative tangential direction per stationary induction element 4. The following constraints have been defined to successfully rotate and magnetically levitate the ring:

$F_z = MG$,
$F_x = 0$,
$F_{na}$ and $F_{nb} \leq 0$,
$\forall = \forall_a = \forall_b$, with M being the total mass of the rotating ring 2 and G being the gravitational acceleration. The first constraint secures the levitation of the ring, the second constraint puts a hold on ring displacement in the x direction. Using EMS (electromagnetic suspension) only results in attracting normal forces. The last constraint is a design preference.

Figure 11:
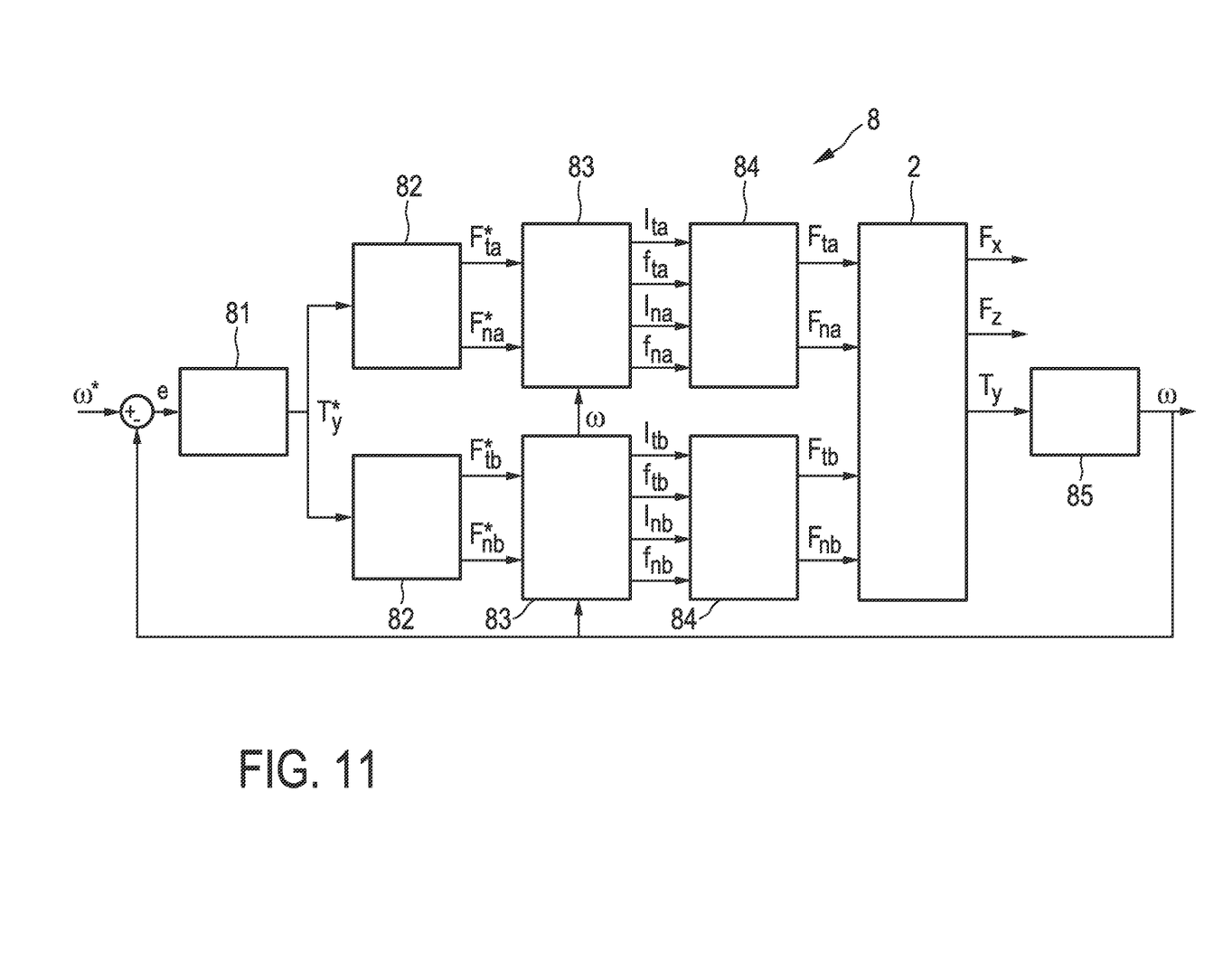
FIG. 11 shows a block diagram of an embodiment of a control scheme according to the present invention.

FIG. 11 illustrates an embodiment of the torque control unit 8 of the overall rotating ring apparatus according to the present invention where a * denotes a reference value. This system does not take into account control of the air gap, but it delivers a pretension of the ring. A motion profile is processed by a controller 81, which produces a reference torque $T^*_y$. For each of the two stationary induction elements 4 shown in FIG. 1 two separate paths are then provided in the control unit 8. Each path comprises of a first block 82 for converting the reference torque $T^*_y$ in two reference forces $F^*_t$, $F^*_n$ (t indicates thrust and n indicates normal; the indices a and b used in FIGS. 1 and 11 distinguish the two stationary induction elements 4). These reference forces are derived having in mind the four constraints defined above. Therefrom, currents I and frequencies f are derived in the decoupled control block 83, from which the actual forces $F_t$, $F_n$, (compare FIG. 1) are obtained in the third block 84. These forces are then acting on the rotating ring 2 as forces $F_x$, $F_z$ and torque $T_y$. The plant block 85 comprises the dynamics of the ring 2 with inclusion of damping due to core losses and air flow resistance.

Figure 12:
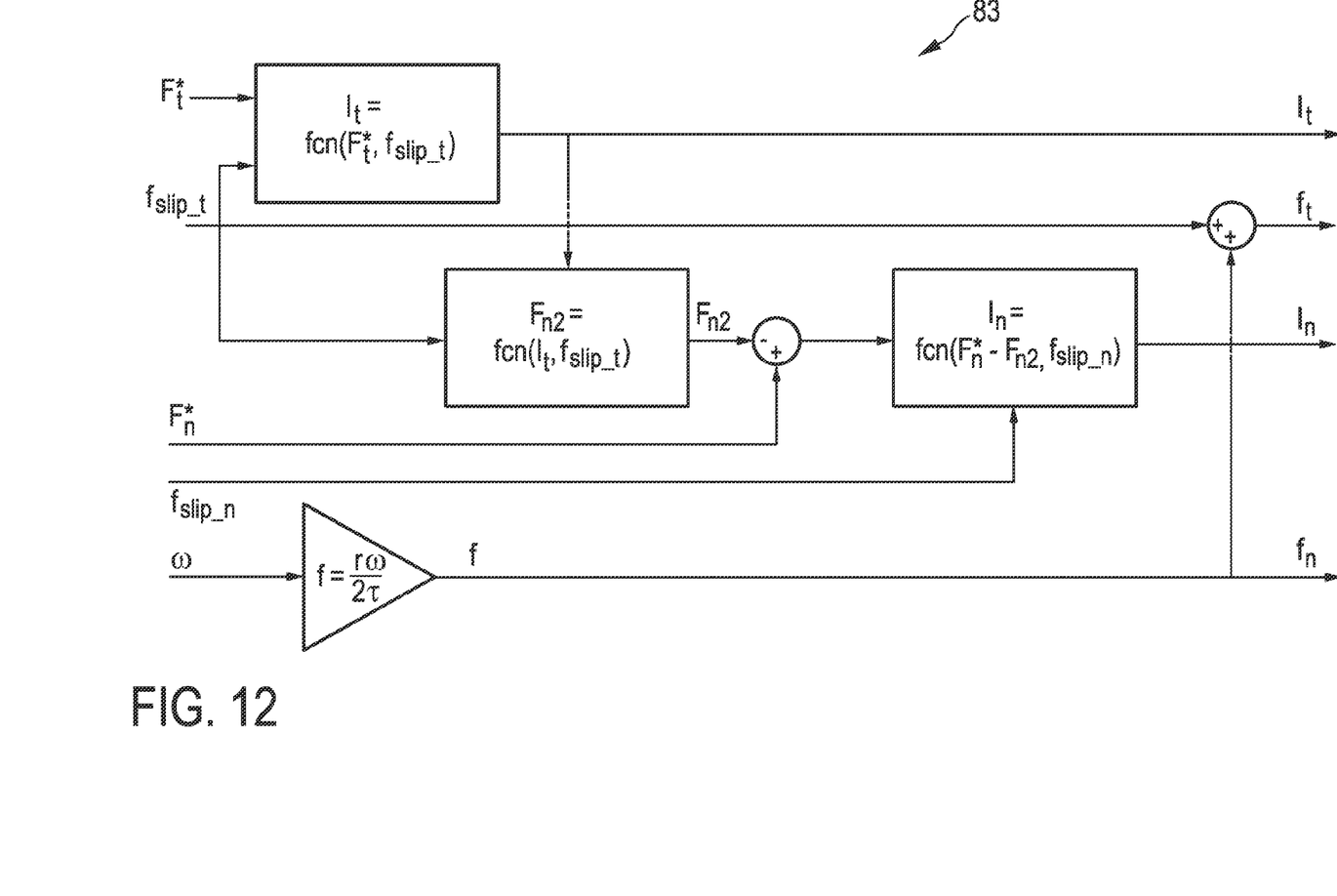
FIG. 12 shows an embodiment of a control unit for decoupled control and of normal and thrust forces.

An essential element of the control unit 8 shown in FIG. 11 is implemented in the blocks 83 "decoupled control SLIM", which is shown in more detail in FIG. 12. This block calculates the values of respectively the thrust and normal LMS currents and frequencies per SLIM. First, the optimal slip frequencies are derived. It can, for instance, be concluded that $f_{slip\_T}$ and $f_{slip\_n}$ are equal to 50 and 0 Hz respectively. Therefore, frequencies above 60 Hz are out of consideration.

The thrust current $I_t$, derived from the inverse fit function, simultaneously produces a normal force $F_{n2}$. Subtraction of this force from the reference normal force $F^*_n$ leads to the calculation of the normal current $I_n$. A mechanical frequency f of the ring is the same as the normal frequency $f_n$, because $f_{slip\_n}$ is set at 0 Hz.

Figure 13:
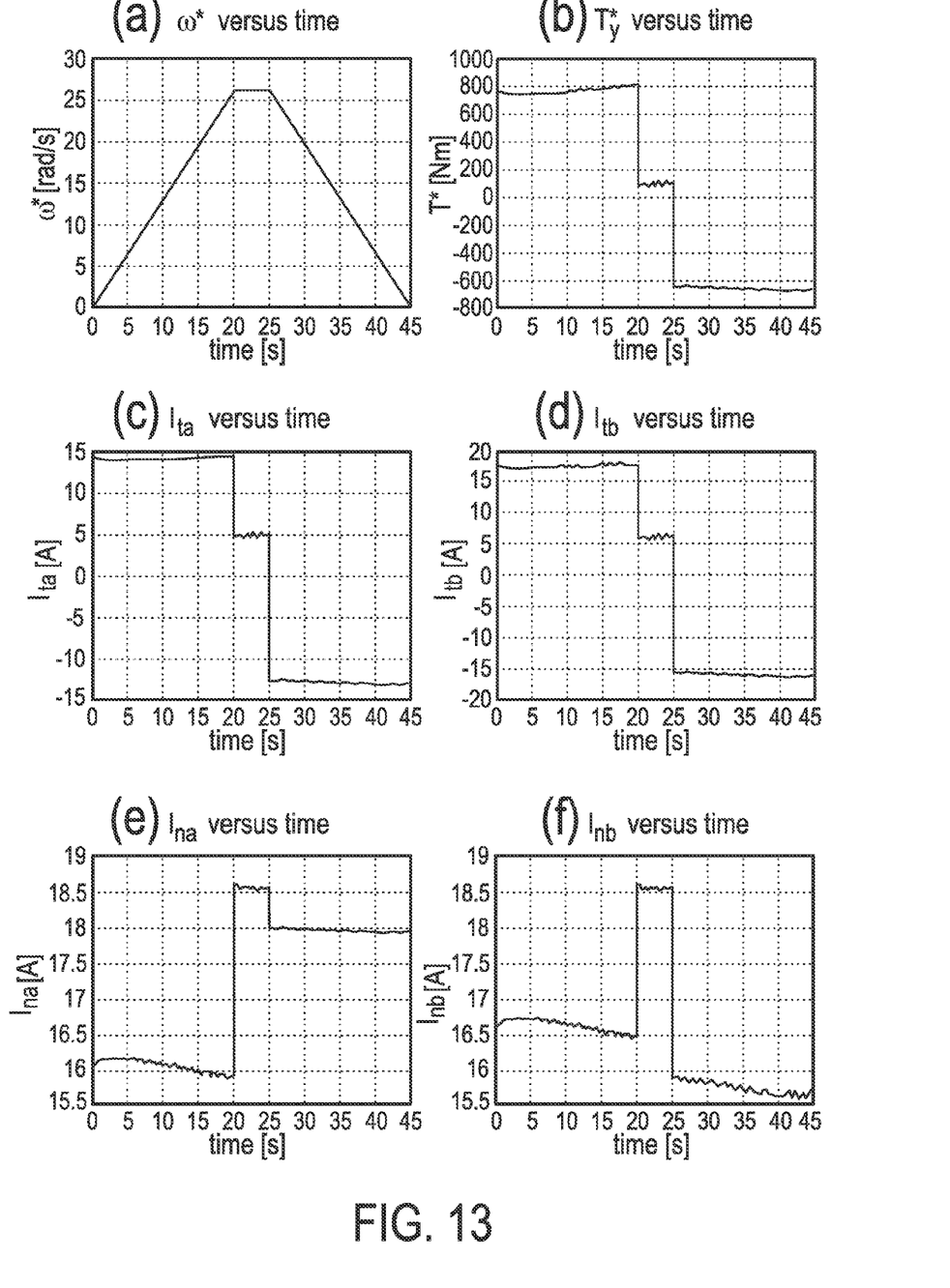
FIG. 13 shows results of a simulation of a rotating ring apparatus according to the present invention.

The number of pole pairs p per SLIM has been increased from 4 to 8, as result, the force performance significantly improves and withstands the mass M of the ring without saturation of currents. The forces, with the air gap g of 1 mm, have been calculated, and a fit has been made on these results. The two SLIMs are placed under an angle $\forall$ of 40° and the results from a simulation are shown in FIG. 13.

The angle $\forall$ of 40° is chosen to fulfill sufficient ring space between the two SLIMs. In other words, the ring space between the two SLIMs is sufficient enough to have no influence of induced eddy currents from one SLIM to the other.

As mentioned above, the air gap between the stationary induction element 4 and the rotating induction element 5 can be controlled by an axial bearing means. Using this bearing means as part of pre-tension results in significant lower primary currents than shown in FIG. 13. As a result, smaller SLIMs with less number of poles could be implemented in the rotating ring apparatus.

According to the present invention a novel rotating ring apparatus is proposed as well as a method of simultaneous and decoupled control of thrust and normal forces. The rotating apparatus using a rotation unit to rotate and levitate a rotating induction element. The system and the control method are simple and straightforward, making it easy to implement in practice. The fact that the thrust force producing current simultaneously generates a normal force is favorably exploited according to the present invention. Preferably, the normal force being currently set at zero slip frequency, which means it does not produce thrust force.

In summary, the present invention provides a rotating ring apparatus which can be used in different application for rotation of an element around a central region. It provides a smart implementation of the attraction forces already developed by linear induction motors and taming these forces to serve the purpose of levitation of the rotating elements, the usage of external magnetic levitation units together with induction motor segments, and an improved manner of simultaneous control of levitation and rotation.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. A rotating ring apparatus comprising:
   a stationary ring,
   a rotating ring for rotation around a central region, wherein the rotating ring is disposed between the stationary ring and the central region,
   a rotation unit for radially bearing and rotating said rotating ring with respect to the stationary ring, said rotation unit including a stationary induction element mounted on said stationary ring and a rotating induction element mounted on said rotating ring, and said rotating induction element is arranged at a larger radial distance from the central region than said stationary induction element, and
   the rotation unit further including an induction motor having a controller arranged to control both the rotation and the levitation of the rotating induction element.

2. The rotating ring apparatus as claimed in claim 1, wherein said stationary induction element comprises one or more arc-shaped induction sub-elements arranged at different angular positions around said central region.

3. The rotating ring apparatus as claimed in claim 2, wherein said one or more induction sub-elements each comprises a ferromagnetic core element, and a plurality of electrically conductive windings wound within core element.

4. The rotating ring apparatus as claimed in claim 3, wherein said one or more induction sub-elements each comprises a single or double layer of windings.

5. The rotating ring apparatus as claimed in claim 3, wherein said ferromagnetic core element has a toothed structure.

6. The rotating ring apparatus as claimed in claim 1, wherein said rotating induction element comprises a closed induction ring.

7. The rotating ring apparatus as claimed in claim 6, wherein said induction ring is made of an electrically conductive material.

8. The rotating ring apparatus as claimed in claim 6, wherein said induction ring comprises a single ring layer made of a single material.

9. The rotating ring apparatus as claimed in claim 6, wherein said induction ring comprises a first ring layer made of a first material, and a second ring layer made of a second material, the induction ring being arranged such that the first ring layer faces said stationary induction element.

10. The rotating ring apparatus as claimed in claim 9, wherein said first material is Al or Cu and the said second material is at least one of ferromagnetic iron or steel.

11. The rotating ring apparatus as claimed in claim 1, further comprising axial bearing means for axially bearing said rotating ring with respect to said stationary ring.

12. The rotating ring apparatus as claimed in claim 1, further comprising a radiation source mounted on said rotating ring for rotation around an object placed in said central region and for emitting radiation in the direction of said object, and a detection unit for detecting radiation passed through said object and said central region.

13. The rotating ring apparatus as claimed in claim 12, wherein said detection unit is mounted on said rotating ring.

14. The rotating ring apparatus as claimed in claim 1, wherein said stationary induction element comprises at least two induction sub-elements arranged at different angular positions around said central region and wherein said controller is adapted to control the frequencies and the currents for control of levitation forces of said induction sub-elements by controlling frequencies and currents provided to said induction sub-elements.

15. The rotating ring apparatus as claimed in claim 1, wherein said rotating induction element protrudes out of a side of the rotating ring.

16. The rotating ring apparatus as claimed in claim 15, wherein said stationary induction element is disposed at the same side of the rotating ring.

17. A rotating ring apparatus, comprising:
    a stationary ring,
    a rotating ring for rotation around a central region, wherein the rotating ring is disposed between the stationary ring and the central region,
    a rotation unit for radially bearing and rotating said rotating ring with respect to the stationary ring, said rotation unit including a stationary induction element mounted on said stationary ring and a rotating induction element mounted on said rotating ring, and
    a permanent magnet motor located within said rotation unit having a controller arranged to rotate and levitate the rotating induction element,
       wherein said rotation unit comprises a radial levitation unit which includes magnetic bearings of two pairs of permanent magnets, a first magnet of each pair mounted on the stationary ring and a second magnet of each pair mounted on the rotating ring to rotate and levitate the induction element.

18. The rotating ring apparatus as claimed in claim 17, wherein said radial levitation unit comprises an active or passive magnetic bearing unit.

19. A rotating ring apparatus, comprising:
    a stationary ring,
    a rotating ring for rotation around a central region, wherein the rotating ring is disposed between the stationary ring and the central region, a rotation unit for radially bearing and rotating said rotating ring with respect to the stationary ring, said rotation unit including a stationary induction element mounted on said stationary ring and a rotating induction element mounted on said rotating ring, and said rotating induction element is arranged at a larger radial distance from the central region than said stationary induction element, and a controller for controlling said rotation unit to rotate and levitate the rotating induction element;

wherein the rotation unit includes an induction motor that controls both the rotation and the levitation of the rotating induction element.

20. The rotating ring apparatus as claimed in claim 19, wherein the rotation unit controls the levitation of the rotating induction element through an attraction force of the induction motor.

\* \* \* \* \*